(12) United States Patent
Lee et al.

(10) Patent No.: US 9,700,374 B2
(45) Date of Patent: Jul. 11, 2017

(54) TUNABLE MICROWAVE ABLATION PROBE (71) Applicant: COVIDIEN LP, Mansfield, MA (US)

(72) Inventors: Anthony C. Lee, Los Altos Hills, CA (US); Kenlyn S. Bonn, Lakewood, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/189,807

(22) Filed: Jun. 22, 2016

(65) Prior Publication Data

US 2016/0296283 A1    Oct. 13, 2016

Related U.S. Application Data

(62) Division of application No. 14/143,897, filed on Dec. 30, 2013, now Pat. No. 9,375,275, which is a division
(Continued)

(51) Int. Cl.
*A61B 18/18*    (2006.01)
*A61B 17/00*    (2006.01)
*A61B 18/00*    (2006.01)

(52) U.S. Cl.
CPC ...... *A61B 18/1815* (2013.01); *A61B 2017/00424* (2013.01); *A61B 2017/00433* (2013.01);
(Continued)

(58) Field of Classification Search
CPC ............ A61B 18/18; A61B 18/1815; A61B 2018/1846; A61B 2018/1823;
(Continued)

(56) References Cited

U.S. PATENT DOCUMENTS

D263,020 S    2/1982   Rau, III
D295,893 S    5/1988   Sharkany et al.
(Continued)

FOREIGN PATENT DOCUMENTS

DE    390937 C    3/1924
DE    1099658 B   2/1961
(Continued)

OTHER PUBLICATIONS

European Search Report EP 09010873.9 extended dated Nov. 13, 2009.
(Continued)

*Primary Examiner* — Thomas Giuliani (57) ABSTRACT

An electromagnetic surgical ablation probe having a tunable helical antenna element includes a coaxial feedline having an inner conductor coaxially disposed within a dielectric, and an outer conductor coaxially disposed around the dielectric. The inner conductor and dielectric extend distally beyond a distal end of the outer conductor. A helical antenna element is operably coupled to a distal end of the inner conductor. During use, the antenna may be tuned by changing at least one dimension of the helical antenna element. Embodiments are presented wherein a dimensions of the helical antenna element is changed by state change of a shape memory alloy, by a change in temperature, by activation of a piston by fluidic pressure, by linear motion of a conical tip, and by a manual screw-type adjustment.

9 Claims, 7 Drawing Sheets

Related U.S. Application Data of application No. 12/713,515, filed on Feb. 26, 2010, now Pat. No. 8,617,153.

(52) U.S. Cl.
CPC ............... *A61B 2017/00867* (2013.01); *A61B 2018/00023* (2013.01); *A61B 2018/00077* (2013.01); *A61B 2018/00142* (2013.01); *A61B 2018/00577* (2013.01); *A61B 2018/1823* (2013.01); *A61B 2018/1846* (2013.01); *A61B 2018/1869* (2013.01); *A61B 2018/1892* (2013.01)

(58) Field of Classification Search
CPC .... A61B 2018/1869; A61B 2018/1876; A61B 2018/1861
USPC ................. 606/33, 42; 607/101, 155, 156
See application file for complete search history.

(56) References Cited

U.S. PATENT DOCUMENTS

| | | | |
|---|---|---|---|
| D295,894 S | 5/1988 | Sharkany et al. | |
| 4,825,880 A * | 5/1989 | Stauffer ............. | A61B 18/1815 607/156 |
| 4,945,912 A | 8/1990 | Langberg | |
| 5,057,106 A | 10/1991 | Kasevich et al. | |
| 5,364,392 A | 11/1994 | Warner et al. | |
| 5,370,644 A | 12/1994 | Langberg | |
| 5,405,346 A | 4/1995 | Grundy et al. | |
| 5,531,662 A | 7/1996 | Carr | |
| 5,693,082 A * | 12/1997 | Warner .............. | A61B 18/1206 606/34 |
| 5,800,494 A | 9/1998 | Campbell et al. | |
| 5,810,803 A | 9/1998 | Moss et al. | |
| 5,957,969 A | 9/1999 | Warner et al. | |
| 5,961,871 A | 10/1999 | Bible et al. | |
| D424,694 S | 5/2000 | Tetzlaff et al. | |
| D425,201 S | 5/2000 | Tetzlaff et al. | |
| 6,245,062 B1 | 6/2001 | Berube et al. | |
| D449,886 S | 10/2001 | Tetzlaff et al. | |
| 6,312,427 B1 | 11/2001 | Berube et al. | |
| 6,364,876 B1 | 4/2002 | Erb et al. | |
| D457,958 S | 5/2002 | Dycus et al. | |
| D457,959 S | 5/2002 | Tetzlaff et al. | |
| 6,512,956 B2 | 1/2003 | Arndt et al. | |
| 6,592,579 B2 | 7/2003 | Arndt et al. | |
| 6,675,050 B2 | 1/2004 | Arndt et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| 7,115,126 B2 | 10/2006 | Berube et al. | |
| D533,942 S | 12/2006 | Kerr et al. | |
| D535,027 S | 1/2007 | James et al. | |
| 7,194,297 B2 | 3/2007 | Talpade et al. | |
| D541,418 S | 4/2007 | Schechter et al. | |
| D541,938 S | 5/2007 | Kerr et al | |
| 7,311,703 B2 | 12/2007 | Turovskiy et al. | |
| D564,662 S | 3/2008 | Moses et al. | |
| 7,387,627 B2 | 6/2008 | Erb et al. | |
| 8,068,921 B2 | 11/2011 | Prakash et al. | |
| 8,280,525 B2 * | 10/2012 | Rusin .................... | A61B 18/18 607/101 |
| 8,617,153 B2 | 12/2013 | Lee et al. | |
| 8,777,939 B2 * | 7/2014 | Lee .................... | A61B 18/1815 606/33 |
| 9,375,275 B2 | 6/2016 | Lee et al. | |
| 2006/0085054 A1 | 4/2006 | Zikorus et al. | |
| 2006/0241576 A1 | 10/2006 | Diederich et al. | |
| 2006/0287649 A1 | 12/2006 | Ormsby et al. | |
| 2008/0266203 A1 | 10/2008 | Rossetto et al. | |
| 2009/0131926 A1 | 5/2009 | Rusin et al. | |
| 2010/0094272 A1 * | 4/2010 | Rossetto ............... | A61B 18/18 606/33 |
| 2011/0213351 A1 | 9/2011 | Lee et al. | |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 A1 | 8/1994 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0836868 A2 | 4/1998 |
| EP | 0882955 A1 | 12/1998 |
| EP | 1159926 A2 | 12/2001 |
| FR | 179607 | 11/1906 |
| FR | 1275415 A | 11/1961 |
| FR | 1347865 A | 1/1964 |
| FR | 2235669 A1 | 1/1975 |
| FR | 2276027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2862813 A1 | 5/2005 |
| FR | 2864439 A1 | 7/2005 |
| JP | 55106 | 1/1993 |
| JP | 0540112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2008142467 A | 6/2008 |

(56) References Cited

FOREIGN PATENT DOCUMENTS

| SU | 166452 | 11/1964 |
|---|---|---|
| SU | 401367 A1 | 10/1973 |
| SU | 727201 A2 | 4/1980 |

OTHER PUBLICATIONS

European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, field Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Charlotte, NC 2003.

(56) References Cited

OTHER PUBLICATIONS

Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.

Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
U.S. Appl. No. 08/483,742, filed Jun. 7, 1995.
U.S. Appl. No. 08/136,098, filed Oct. 14, 1991.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.

(56) References Cited

OTHER PUBLICATIONS

European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
Kennedy et al., "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Longterm Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.

(56) References Cited

OTHER PUBLICATIONS

Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817825.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.

\* cited by examiner

TUNABLE MICROWAVE ABLATION PROBE

CROSS-REFERENCE TO RELATED APPLICATIONS

This application is a divisional application of U.S. patent application Ser. No. 14/143,897, filed on Dec. 30, 2013, now U.S. Pat. No. 9,375,275, which is a divisional application of U.S. patent application Ser. No. 12/713,515, filed on Feb. 26, 2010, now U.S. Pat. No. 8,617,153, the entire contents of all of which are incorporated by reference herein.

BACKGROUND

1. Technical Field

The present disclosure relates to systems and methods for providing energy to biological tissue and, more particularly, to a microwave ablation surgical antenna having a tunable or adjustable helical coil, and methods of use and manufacture thereof.

2. Background of Related Art

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the helix length, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna tuning, antenna impedance and tissue impedance. Tissue impedance may change during an ablation procedure due to a number of factors, e.g., tissue denaturization or desiccation occurring from the absorption of microwave energy by tissue. Changes in tissue impedance may cause an impedance mismatch between the probe and tissue, which may affect delivery of microwave ablation energy to targeted tissue.

SUMMARY

The present disclosure is directed to a microwave ablation probe having a self-tuning, or adjustable, helical antenna element. The helical antenna element may be tuned dynamically and automatically during use, and/or may be tuned manually.

In one embodiment, a helical antenna element is formed from shape memory alloy (SMA). SMAs are a family of alloys having anthropomorphic qualities of memory and trainability. One of the most common SMAs is Nitinol which can retain shape memories for two different physical configurations and changes shape as a function of temperature. Recently, other SMAs have been developed based on copper, zinc and aluminum and have similar shape memory retaining features.

SMAs undergo a crystalline phase transition upon applied temperature and/or stress variations. A particularly useful attribute of SMAs is that after it is deformed by temperature/stress, it can completely recover its original shape on being returned to the original temperature. This transformation is referred to as a thermoelastic martenistic transformation.

Under normal conditions, the thermoelastic martenistic transformation occurs over a temperature range which varies with the composition of the alloy itself, and the type of thermal-mechanical processing by which it was manufactured. In other words, the temperature at which a shape is "memorized" by an SMA is a function of the temperature at which the martensite and austenite crystals form in that particular alloy. For example, nickel titanium alloys (NiTi), commonly known as Nitinol, can be fabricated so that the shape memory effect will occur over a wide range of temperatures, e.g., −2700° to +1000° Celsius.

A dimension of the helical coil, e.g., the coil span (e.g., the distance between helical turns) and/or the diameter of the helical antenna element may be configured to change upon transformation of the SMA material from an austenitic state to a martenistic state in response to temperature changes at the surgical site. In some embodiments, a dimension of the helical coil may be configured to change in response to mechanical actuation, such as without limitation, actuation of a piston, actuation member (e.g., the inner conductor), and/or an adjustment ring. A change in antenna tuning associated with higher temperatures is thus corrected by a corresponding dimensional change in the helical antenna element triggered by the higher temperature. The helical coil antenna may be continuously and/or infinitely adjustable.

In some embodiments, an ablation probe in accordance with the present disclosure includes an inner conductor, a dielectric coaxially disposed around the inner conductor, and an outer conductor coaxially disposed around the dielectric. The dielectric and the inner conductor extend distally from the outer conductor. A tunable helical antenna element is coaxially disposed about the distal extension of the dielectric and is operably joined at a distal end thereof to the inner conductor. The tunable helical antenna element has a first dimension corresponding to a first tuning and at least a second dimension corresponding to a second tuning.

In other embodiments, an ablation probe in accordance with the present disclosure includes a generally tubular inner conductor, a dielectric coaxially disposed around the inner conductor, and an outer conductor coaxially disposed around the dielectric. The dielectric and the inner conductor extend distally from the outer conductor. A helical slot is defined in at least one of the dielectric or inner conductor. A tunable helical antenna element is coaxially disposed about the distal extension of the dielectric and is operably joined at a distal end thereof to the inner conductor. The tunable helical antenna element has a first dimension corresponding to a first tuning and at least a second dimension corresponding to a second tuning. A piston is slidably disposed within the inner conductor, wherein a proximal end of the helical antenna element is operably coupled to a distal end of the piston through the helical slot.

In yet other embodiments, an ablation probe in accordance with the present disclosure includes a dielectric, and an inner conductor coaxially disposed within the dielectric and longitudinally movable with respect the dielectric. The inner conductor extends distally from the dielectric. An outer conductor is coaxially disposed around the dielectric, and the dielectric extends distally from the outer conductor. The disclosed probe includes a tip fixed to a distal end of the inner conductor, a biasing member configured to bias the tip distally, and a tunable helical antenna element coaxially disposed about the distal extension of the dielectric and operably joined at a distal end thereof to the inner conductor. The tunable helical antenna element has a first dimension corresponding to a first tuning, and at least a second dimension corresponding to a second tuning.

In still other embodiments, an ablation probe in accordance with the present disclosure includes an inner conductor, a dielectric coaxially disposed around the inner conductor, and an outer conductor coaxially disposed around the dielectric. The dielectric and the inner conductor extend distally from the outer conductor. A barrel is coaxially disposed about the outer conductor and is movable along a longitudinal axis thereof. The barrel includes an exterior threaded portion, an adjustment collar rotatable about a longitudinal axis thereof, and has an interior threaded portion adapted to cooperatively engage the exterior threaded portion of the barrel. A tunable helical antenna element is coaxially disposed about the distal extension of the dielectric and is operably joined at a distal end thereof to the inner conductor and operably joined at a proximal end thereof to the barrel. The tunable helical antenna element has a first dimension corresponding to a first tuning, and at least a second dimension corresponding to a second tuning.

A method for tuning an electromagnetic surgical ablation probe is also disclosed which includes the steps of providing an electromagnetic surgical ablation probe and changing at least one dimension of the helical antenna element provided therein. The provided electromagnetic surgical ablation probe includes an inner conductor, a dielectric coaxially disposed around the inner conductor, an outer conductor coaxially disposed around the dielectric, wherein the dielectric and the inner conductor extend distally from the outer conductor, and a helical antenna element coaxially disposed about the distal extension of the dielectric and operably joined at a distal end thereof to the inner conductor.

Also disclosed in an electromagnetic surgical ablation system that includes a source of ablation energy, and a tunable electromagnetic surgical ablation probe operably coupled to the source of ablation energy. The tunable electromagnetic surgical ablation probe includes an inner conductor, a dielectric coaxially disposed around the inner conductor, and an outer conductor coaxially disposed around the dielectric. The dielectric and the inner conductor extend distally from the outer conductor. The probe further includes a helical antenna element coaxially disposed about the distal extension of the dielectric that is operably joined at a distal end thereof to the inner conductor. The helical antenna element is tunable by changing at least one changeable dimension thereof, including without limitation gap distance, distance between turns, length, and diameter.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described hereinbelow with reference to the accompanying drawings; however, the disclosed embodiments are merely examples of the disclosure, which may be embodied in various forms. Well-known or repetitive functions, constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 1:
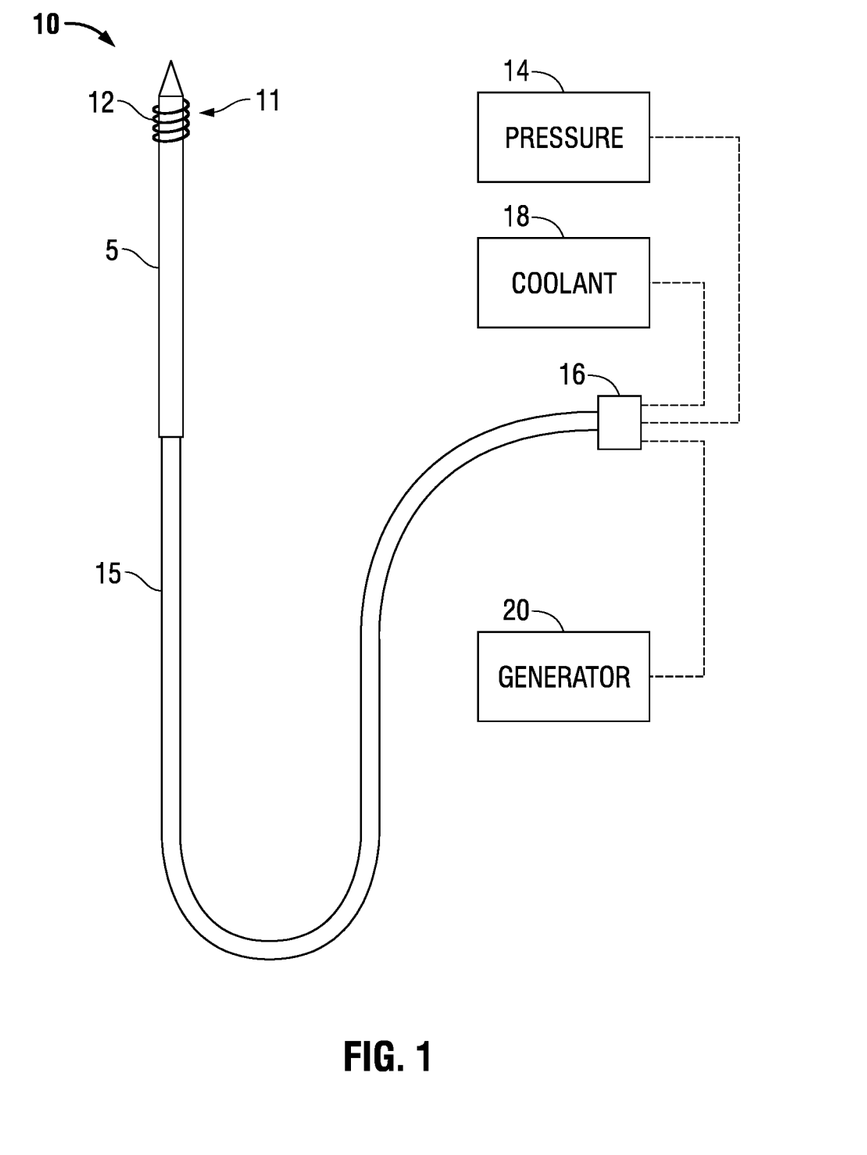
FIG. 1 is a diagram of a microwave ablation system having a surgical ablation probe in accordance with an embodiment of the present disclosure.

FIG. 1 shows an embodiment of a microwave ablation system 10 in accordance with the present disclosure. The microwave ablation system 10 includes an electromagnetic surgical ablation probe 5 connected by a cable 15 to connector 16, which may further operably connect the antenna probe 10 to a generator assembly 20. Probe 5 includes a distal radiating portion 11 having a helical antenna element 12. Generator assembly 20 may be any suitable source of ablation energy, e.g., microwave or RF energy in the range of about 500 MHz to about 10 GHz. In some embodiments, generator assembly 20 may provide ablation energy in a range of about 915 MHz to about 2.45 GHz. Cable 15 may additionally or alternatively provide a conduit (not explicitly shown) configured to provide coolant from a coolant source 18 and/or a pressure source 14 to the electromagnetic surgical ablation probe 10. Pressure source 14 may be configured to provide pneumatic pressure (e.g., compressed air or other gas), but it is envisioned any suitable pressurized media may be provided by pressure source 14.

Figure 2A:
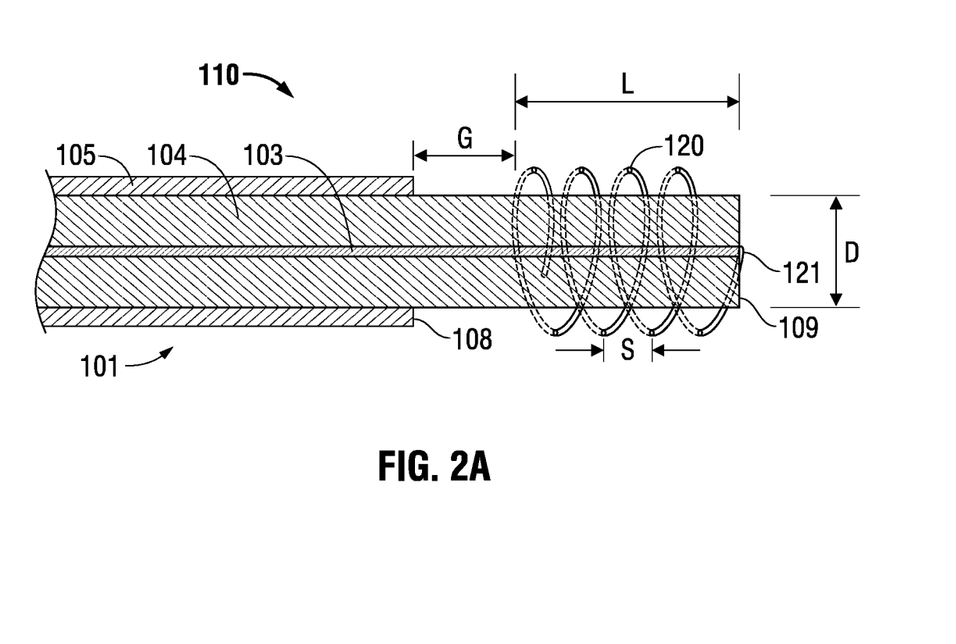
FIG. 2A is a cross sectional, side view of an embodiment of a surgical ablation probe having a helical antenna assembly in accordance with the present disclosure.
Figure 2B:
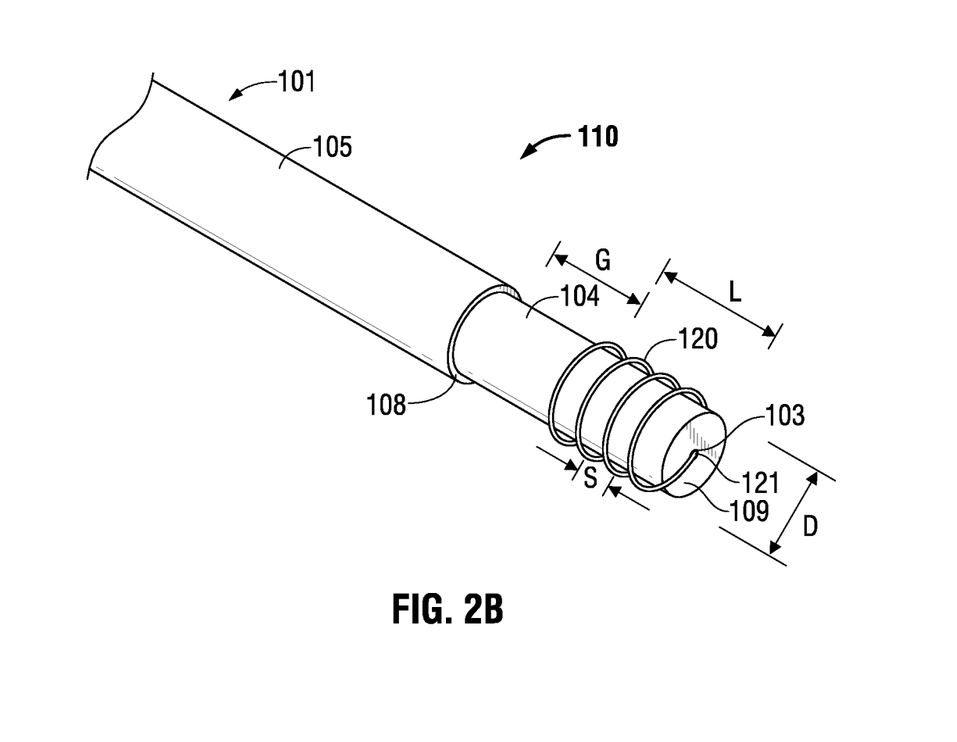
FIG. 2B is a perspective view of the surgical ablation probe of FIG. 2A.

With reference to FIGS. 2A and 2B, a microwave ablation probe 110 includes a shaft assembly 101 having an inner conductor 103, a dielectric 104 coaxially disposed about the inner conductor 103, and an outer conductor 105 coaxially disposed about the dielectric 104. Inner conductor 103 and outer conductor 105 may be formed from any suitable heat-resistant electrically conductive material, including without limitation stainless steel. Inner conductor 103 and outer conductor 105 may be plated or clad with a biocompatible, electrically-conductive material, which may improve the electrical conductivity of the inner conductor 103 and outer conductor 105. In some embodiments, inner conductor 103 and outer conductor 105 may be plated or clad with silver. Dielectric 104 may be formed from any suitable heat-resistant material having electrically insulative properties, e.g., ceramic, porcelain, or polymeric material. Inner conductor 103 and dielectric 104 extend distally beyond a distal end 108 of outer conductor 105. A distal end 121 of inner conductor 103 is exposed at a distal end 109 of dielectric 104. Helical antenna element 120 is disposed coaxially around a distal region of dielectric 104. A distal end of antenna element 120 is electromechanically joined to inner conductor 103 at the exposed distal end 121 thereof by any suitable manner of joining, including without limitation laser welding, brazing, threaded coupler, and/or crimping. A proximal end of helical antenna element 120 may be detached (e.g., free-floating) to enable helical antenna element 120 to expand and/or contract as discussed in detail below.

Helical antenna element 120 may be formed from material that expands and/or contracts in response to changes in temperature, including without limitation, an SMA alloy such as nickel titanium (NiTi), commonly known as Nitinol. During manufacture, helical antenna element 120 may be formed from Nitinol wire by, e.g., winding the Nitinol wire stock around a form having a generally cylindrical shape; annealing the helical antenna element 120 to define the austenite shape and size thereof; and deforming (e.g., expanding or contracting) the helical antenna element 120 to define the martensite size and shape of helical antenna element 120. In this manner, the desired hot (austenite) and cold (martensite) shapes of helical antenna element 120 may be imprinted into the crystalline structure of the Nitinol wire.

In use, it is believed that an increase in reflections that occur as a result of tissue desiccation and/or denaturization causes an increase in probe temperature. This, in turn, heats helical antenna element 120 and causes the size and/or shape thereof to change and, thus, adjusts and/or corrects the tuning of helical antenna element 120. In particular, tuning may be affected by the gap distance "G" between a distal end of the outer conductor and a proximal end of the helical antenna element 120, the distance "S" between turns of the helical antenna element 120, the length "L" of the helical antenna element 120, and/or the diameter "D" of the helical antenna element 120. The probe 110, shaft 101, and/or distal end 109 may be coated with a lubricious material, such as without limitation, polytetrafluoroethylene (a.k.a. PTFE or Teflon®, manufactured by the E.I. du Pont de Nemours and Co. of Wilmington, Del., USA), polyethylene teraphthalate (PET), or the like.

Figure 3A:
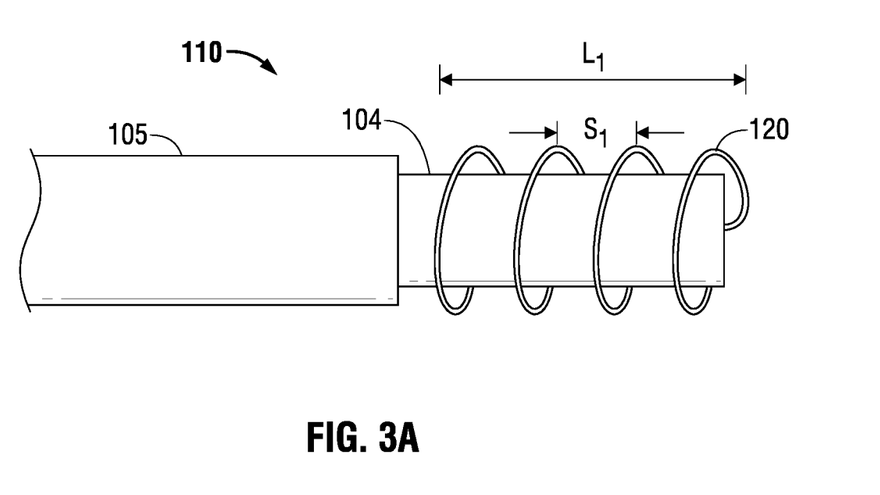
FIG. 3A shows a side view of the surgical ablation probe of FIG. 2A wherein the helical antenna is in a first state.
Figure 3B:
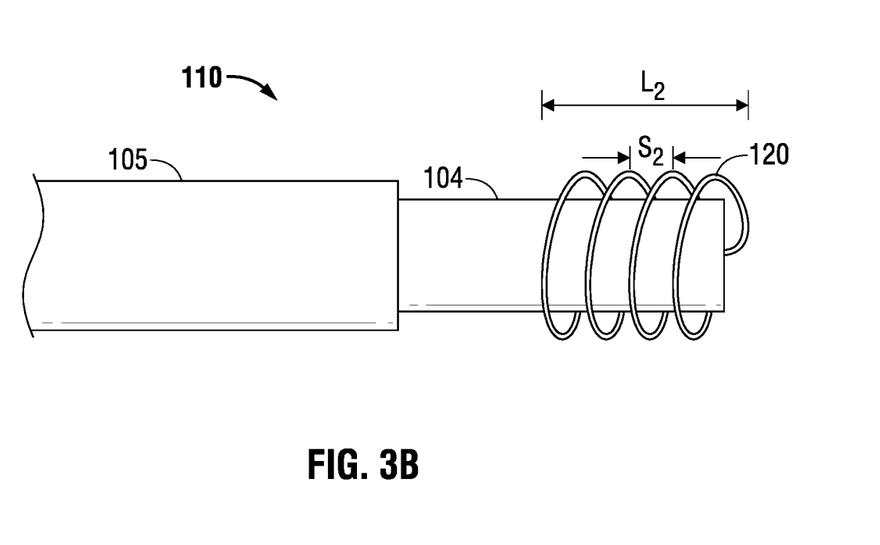
FIG. 3B shows a side view of the surgical ablation probe of FIG. 2A wherein the helical antenna is in a second state.

FIGS. 3A and 3B depict helical antenna element 120 in an austenite state and a martensite state, respectively. In use, heat generated during a microwave ablation surgical procedure causes an increase in temperature in the helical coil and/or associated components of the probe 110, which, in turn, causes the helical antenna element 120 to transition between a martensite shape and size thereof, as best seen in FIG. 3A, and an austenite size and shape thereof, as best seen in FIG. 3B. As shown, helical antenna element 120 is configured such that an increase in temperature results in a decrease in coil length L due to the Nitinol phase transformation. It is also contemplated that helical antenna element 120 is configured such that an increase in temperature results in a decrease in coil diameter D. It is further contemplated that that helical antenna element 120 may be configured such that an increase in temperature results in an increase of length L and/or diameter D. In an embodiment this may be achieved by, e.g., annealing helical antenna element 120 during manufacture to imprint the desired (larger) austenite share thereupon. It is further contemplated that a multiple phase shape metal alloy, e.g., an SMA having more than two primary states may be used to construct helical antenna element 120.

Figure 4A:
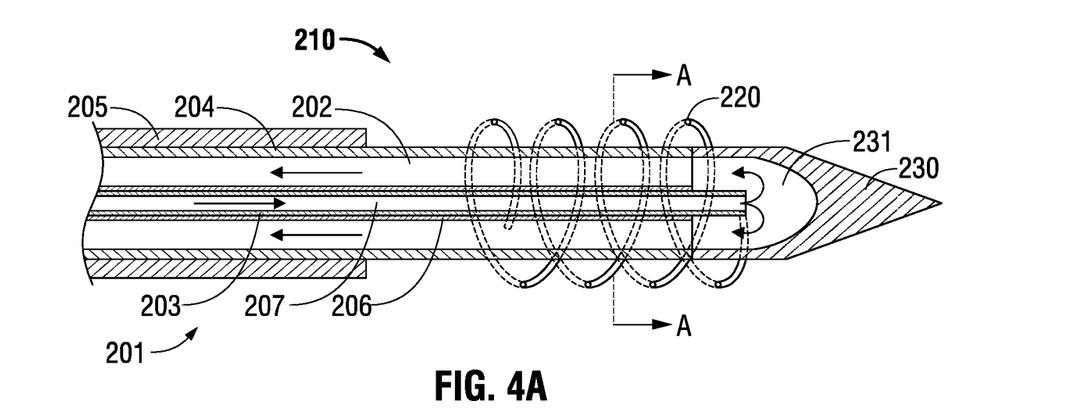
FIG. 4A is a cross sectional side view of another embodiment of a surgical ablation probe having a helical antenna assembly in accordance with the present disclosure.
Figure 4B:
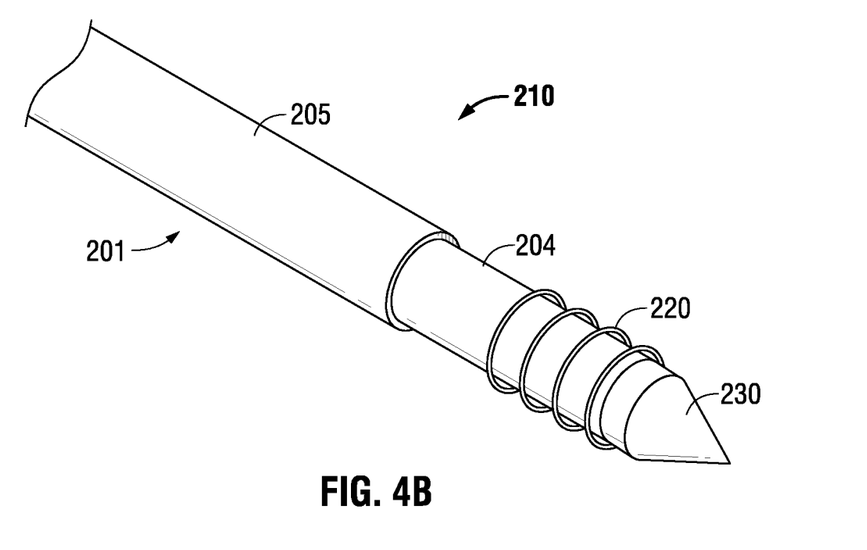
FIG. 4B is a perspective view of the surgical ablation probe of FIG. 4A.
Figure 4C:
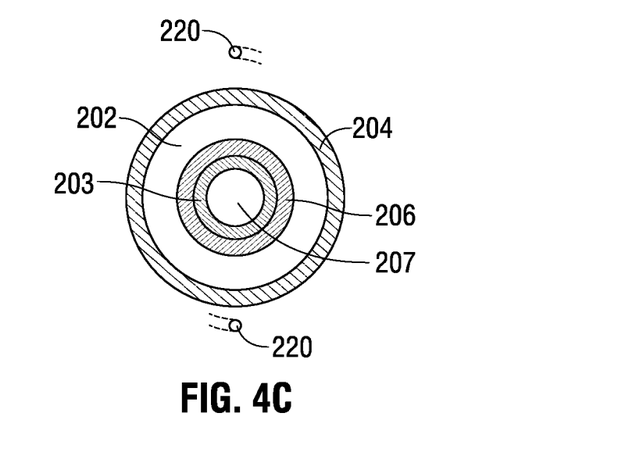
FIG. 4C is a sectional view of the surgical ablation probe of FIG. 4A.

Turning to FIGS. 4A and 4B, a microwave ablation probe 210 in accordance with another embodiment of the present disclosure is shown having a shaft 201 that includes a hollow inner conductor 203, which may have a tubular or other suitable shape. The hollow interior of inner conductor 203 defines an inflow conduit 207 that is adapted to deliver a fluid generally to the shaft, and more specifically, to a tip 230, and to an outflow conduit 202. Any suitable fluid having a low dielectric constant may be utilized, including without limitation water, deionized water, saline, and/or biocompatible oils or gases. Shaft 201 also includes an outer dielectric 204 coaxially disposed about coolant outflow conduit 202, an inner dielectric 206 axially disposed about inner conductor 203, and an outer conductor 205 coaxially disposed about the outer dielectric 204. Outflow conduit 202 is defined by the region between outer dielectric 204 and inner dielectric 206. Tip 230 is fixed to a distal end of outer dielectric 204 and may include a fluid chamber 231 defined therein.

In use, according to one embodiment, coolant flows distally through inflow conduit 207 from coolant source 18, into fluid chamber 231, and flows proximally through outflow conduit 202. Additionally or alternatively, coolant flow may be reversed, e.g., flowing distally though outflow conduit 202 and proximally through inflow conduit 207. Probe 210 may include a sensor (not explicitly shown) that is operably coupled at least one of generator 20 or coolant source 18 and is adapted to sense a surgical parameter, such as without limitation probe temperature and/or tissue impedance. Generator 20 and/or coolant source 18 may be configured to receive a sensed surgical parameter and regulate the flow of ablation energy and/or coolant in response thereto. In this manner, the temperature of helical antenna element 220 may be regulated and, in turn, cause the size and/or shape of helical antenna element 220 to change, thus adjusting and/or correcting the tuning of helical antenna element 220.

Figure 5A:
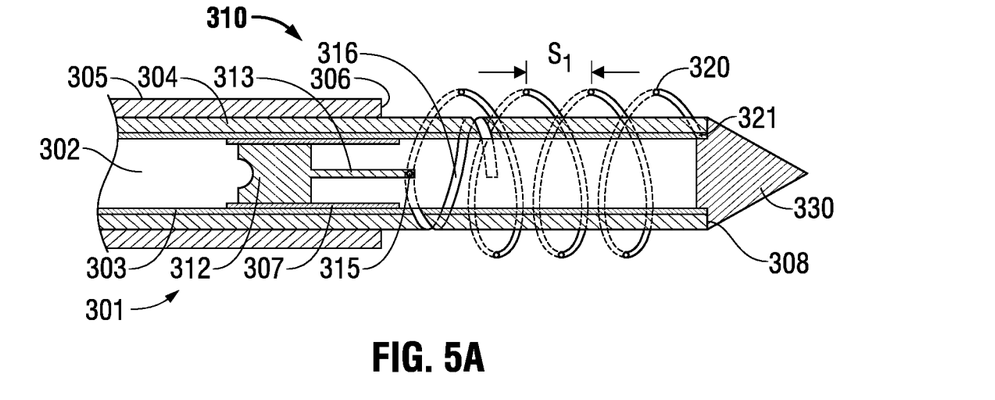
FIG. 5A is a cross sectional side view of another embodiment of a surgical ablation probe having a helical antenna assembly in accordance with the present disclosure, wherein the helical antenna is in a first state.
Figure 5B:
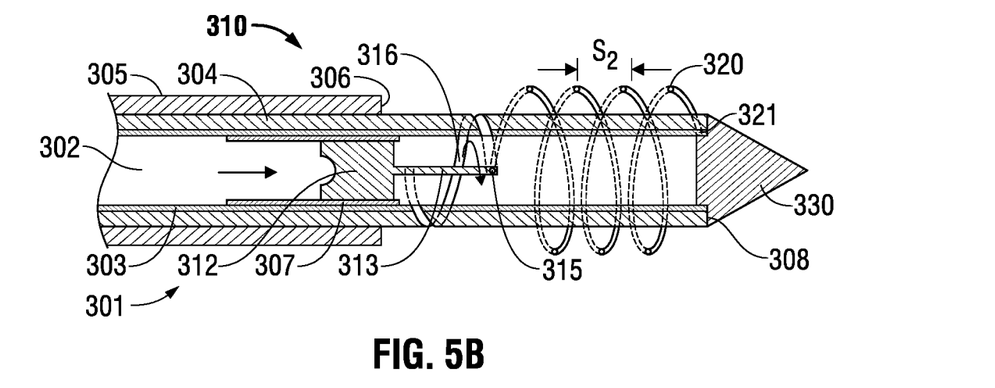
FIG. 5B is a cross sectional side view of the surgical ablation probe of FIG. 5A wherein the helical antenna is in a second state.
Figure 5C:
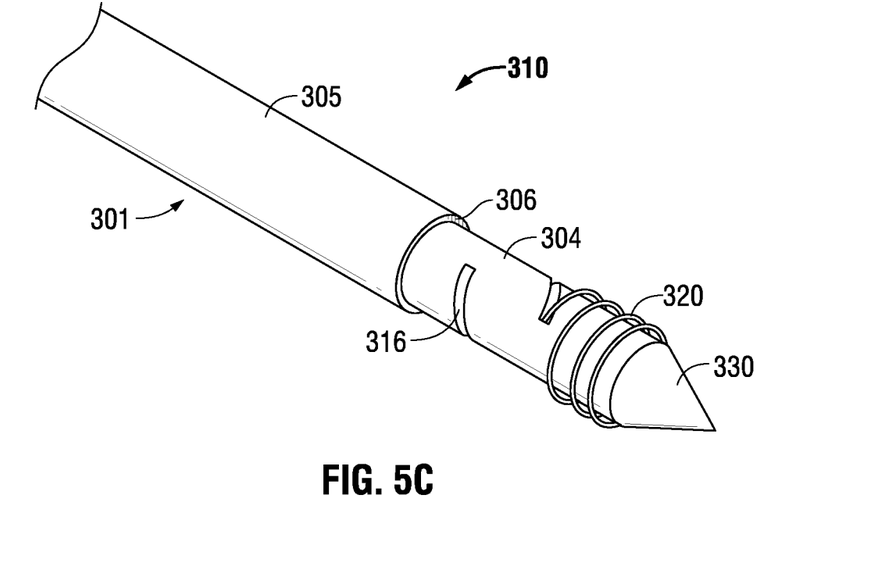
FIG. 5C is a perspective view of the surgical ablation probe of FIG. 5A.

Referring to FIGS. 5A, 5B, and 5C, a microwave ablation probe 310 in accordance with yet another embodiment of the present disclosure is shown. The probe 310 includes a shaft 301 having therein a piston 312 that is slidably disposed longitudinally within a sleeve 307. The shaft 301 includes a tubular outer conductor 305 that is coaxially disposed around a tubular inner conductor 303 having a tubular dielectric 304 disposed therebetween. In some embodiments, a diameter of sleeve 307 may be about the same as a diameter of inner conductor 303. Dielectric 304 and inner conductor 303 extend distally beyond a distal end of outer conductor 305. A tip 330, which may be substantially conical in shape to improve ease of insertion of the probe into tissue, is fixed at a distal end 308 of dielectric 304. Piston 312 is dimensioned to slide and/or rotate freely within sleeve 307 while maintaining a substantially gas-tight or liquid-tight seal therebetween. Piston 312 includes a support 313 that extends distally from a distal end of piston 312 and includes a coupling pin 315 that operably engages a proximal end of helical antenna element 320 through a helical slot 316 defined in dielectric 304 and inner conductor 303. A distal end of helical antenna 320 is coupled to a distal end 321 of inner conductor 303. Piston 312 may be actuated by media, e.g., gas and/or liquid, that is introduced into and/or withdrawn from plenum 302. Any suitable media may be utilized, for example and without limitation, water, saline, air, oxygen, nitrogen, carbon dioxide, and/or biocompatible oil.

In use, media is introduced into, and/or withdrawn from, plenum 302, driving piston 312 distally. As piston 312 traverses distally, coupling pin 315 rides within helical slot 316 and compresses helical antenna element 320 to adjust the tuning thereof. A sensor (not explicitly shown) may be included within probe 310 to sense a physical or surgical parameter related thereto, including without limitation plenum pressure, probe temperature, and/or tissue impedance. Generator 20 and/or pressure source 14 may be configured to receive a sensed surgical parameter and regulate ablation energy and/or plenum pressure in response thereto. In this manner, the tuning of helical antenna element 320 may be regulated and, in turn, cause the size and/or shape of helical antenna element 320 to change, thus adjusting and/or correcting the tuning of helical antenna element 320.

Figure 6A:
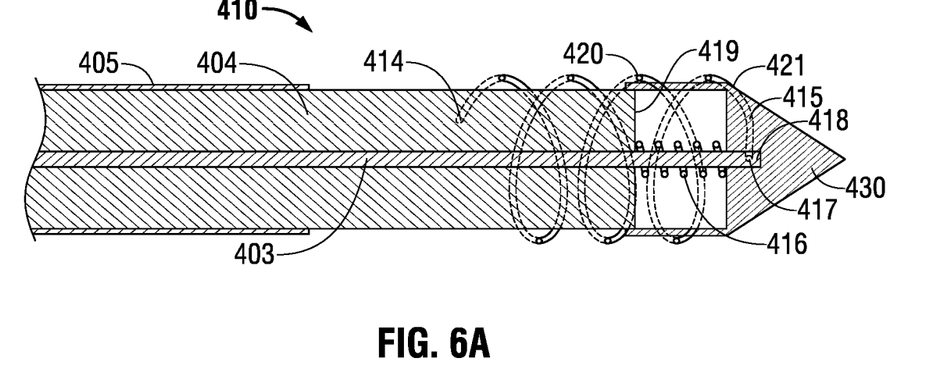
FIG. 6A is a cross sectional side view of yet another embodiment of a surgical ablation probe having a helical antenna assembly in accordance with the present disclosure, wherein the helical antenna is in a first state.
Figure 6B:
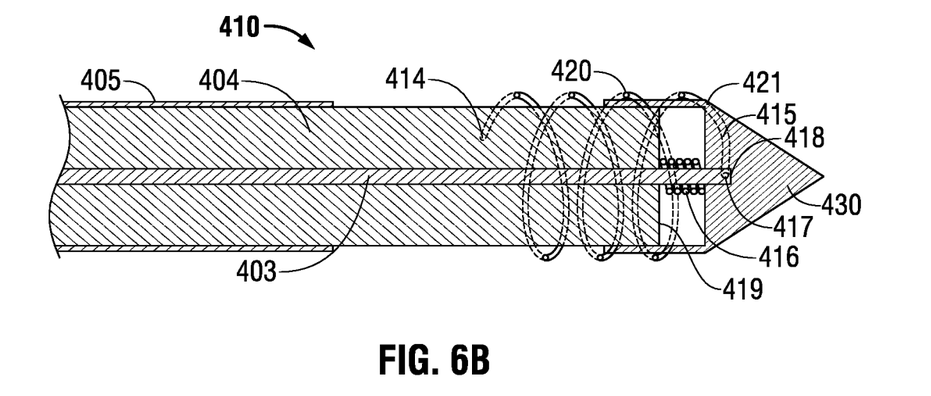
FIG. 6B is a cross sectional side view of the surgical ablation probe of FIG. 6A wherein the helical antenna is in a second state.
Figure 6C:
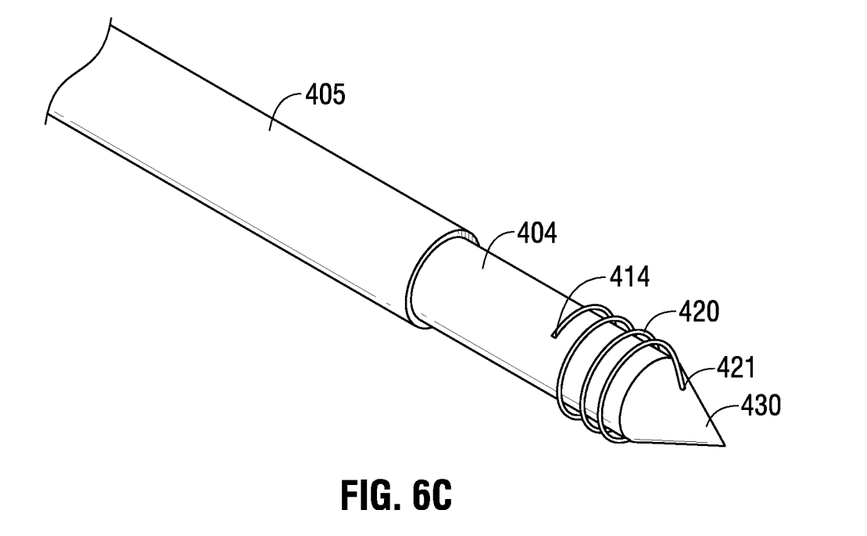
FIG. 6C is a perspective view of the surgical ablation probe of FIG. 6A.

Turning to FIGS. 6A, 6B, and 6C, a microwave ablation probe in accordance with still another embodiment of the present disclosure is shown wherein a probe 410 includes a spring-loaded tip 430. The probe 410 includes a tubular outer conductor 405 that is coaxially disposed around an inner conductor 403 having a dielectric 404 disposed therebetween. Inner conductor 403 is slidably disposed within dielectric 404 and may be operably coupled at a proximal end thereof to an actuator (not explicitly shown) that imparts longitudinal motion to inner conductor 403. For example, and without limitation, an actuator may include a lever, a handle, a threaded adjustment device (e.g., a thumbscrew), or an electromechanical actuator, such as a solenoid, servo, and/or a stepper motor. Inner conductor 403 extends distally beyond a distal end 419 of dielectric 404, and is coupled at a distal end 418 thereof to tip 430 by any suitable manner of attachment, including without limitation, welding, brazing, crimping, clamping, adhesive, and threaded attachment. A biasing member 416 is disposed between tip 430 and distal end 419 of dielectric 404 and is configured to bias tip 430 away from distal end 419 of dielectric 404, e.g., distally therefrom.

Probe 410 includes a helical antenna element 420 that is operably coupled at a distal end thereof to a distal end 418 of inner conductor 403. Additionally or alternatively, helical antenna element 420 may be coupled to inner conductor 403 via lead wire 415 which extends from inner conductor 403 to a surface of tip 430, where lead wire 415 may be joined to helical antenna element 420 at junction 421. A proximal end of helical antenna element 420 may be fixed to dielectric 404 at an outer surface thereof by any suitable manner of attachment. Probe 410 may include a positive stop (not explicitly shown) that is configured to retain the combination of tip 430, biasing member 416, and/or inner conductor 403 to dielectric 404 such that full extension of spring 416 does not cause separation of tip 430, spring 416, and/or inner conductor 403 from dielectric 404. In an embodiment, the actuator (not explicitly shown) may limit distal movement of inner conductor 403 to prevent separation of tip 430, biasing member 416, and/or inner conductor 403 from dielectric 404. During use, helical antenna element 430 may be tuned by causing inner conductor 403 to move longitudinally, e.g., by using an aforesaid actuator to cause inner conductor 403 to move proximally and/or distally, until a desired tuning is achieved.

Figure 7A:
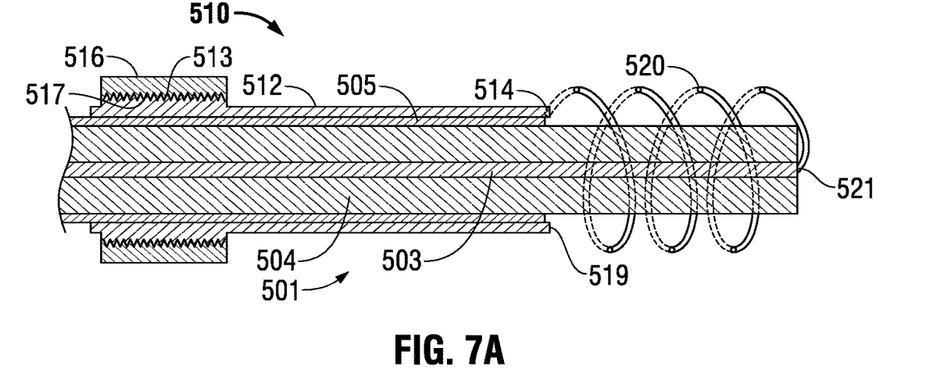
FIG. 7A is a cross sectional side view of still another embodiment of a surgical ablation probe having a helical antenna assembly in accordance with the present disclosure, wherein the helical antenna is in a first state.
Figure 7B:
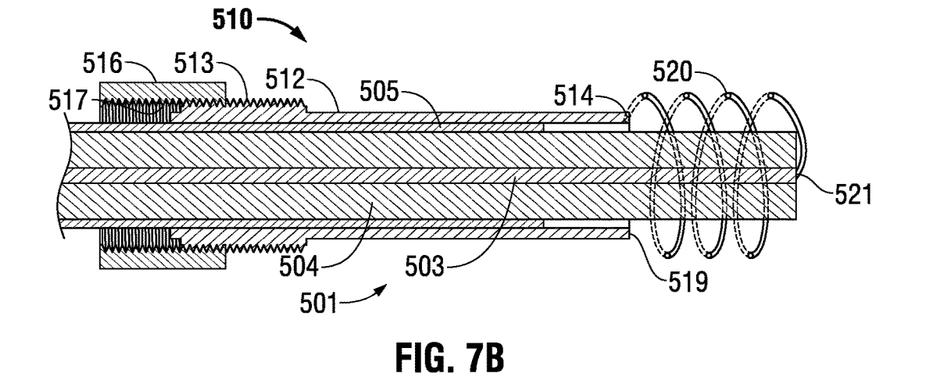
FIG. 7B is a cross sectional side view of the surgical ablation probe of FIG. 7A wherein the helical antenna is in a second state.
Figure 7C:
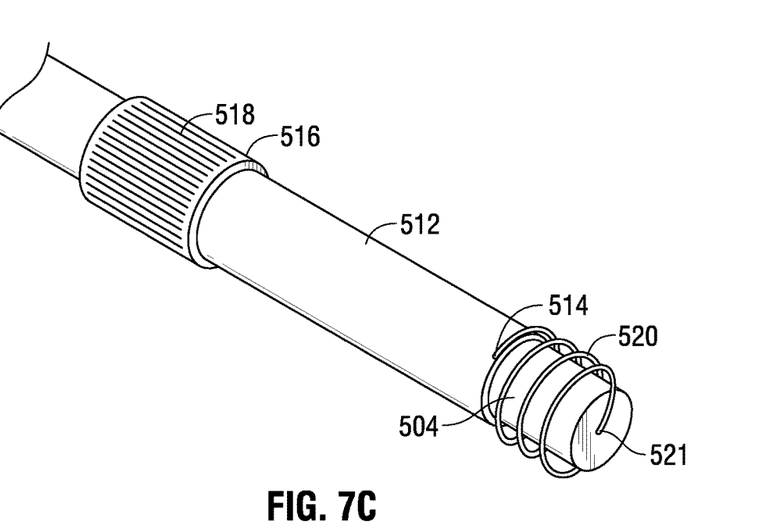
FIG. 7C is a perspective view of the surgical ablation probe of FIG. 7A.

With reference now to FIGS. 7A, 7B, and 7C, disclosed is a microwave ablation probe 510 having a manually-adjustable helical antenna element 520 disposed at a distal end thereof. Probe 510 includes a shaft 501 having an outer conductor 505 that is coaxially disposed around an inner conductor 503 with a dielectric 504 disposed therebetween. Dielectric 504 and inner conductor 503 extend distally beyond a distal end of outer conductor 505. Probe 510 includes an outer barrel 512 that is coaxially disposed around at least outer conductor 505 and includes an exterior threaded portion 513 at a proximal end of outer barrel 512. Exterior threaded portion 513 is configured to operably engage adjustment collar 516 which has an interior threaded portion 517. Adjustment collar 516 may include one or more ergonomic and/or friction enhancing elements 518 to facilitate handling, e.g., scallops, protuberances, knurling, elastomeric material, etc.

A distal end of helical antenna element 520 is operably coupled to a distal end 521 of inner conductor 503. A proximal end of helical antenna element 520 is fixed to a distal end 519 of outer barrel 512. During use, a user (e.g., a surgeon) may adjust the tuning of helical antenna element 520 by rotating adjustment collar 516 to cause outer barrel 512 to move distally and/or proximally to achieve a desired tuning. One or more stop members (not explicitly shown) may be included to maintain outer barrel 512 and/or adjustment collar 516 in cooperative orientation, e.g., to ensure translation of rotational motion of adjustment collar 516 into the desired linear longitudinal motion of outer barrel 512.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A method for tuning an ablation probe, the method comprising:
   supplying energy to an ablation probe including:
      an inner conductor;
      an inner dielectric coaxially-disposed around the inner conductor;
      an outer conductor coaxially-disposed around the inner dielectric, wherein the inner dielectric and the inner conductor extend distally from the outer conductor; and
      a helical antenna element coaxially-disposed about a distal portion of the inner dielectric and coupled to the inner conductor; and
   adjusting a dimension of the helical antenna element by rotating an adjustment collar to tune the ablation probe.

2. The method for tuning an ablation probe in accordance with claim 1, wherein adjusting the dimension of the helical antenna element includes moving at least a portion of the helical antenna element longitudinally relative to the inner conductor.

3. The method for tuning an ablation probe in accordance with claim 1, wherein the dimension of the helical antenna element that is adjusted is selected from the group consisting of a diameter of the helical antenna element, a length of the helical antenna element, a pitch of the helical antenna element, a distance between coils of the helical antenna element, a distance between a proximal end of the helical antenna element and a distal end of the outer conductor, and a position of the helical antenna element relative to a distal end of the inner dielectric.

4. A method for tuning an ablation probe, the method comprising:
   supplying energy to an ablation probe including:
      an inner conductor;
      a dielectric coaxially-disposed around the inner conductor;
      an outer conductor coaxially-disposed around the dielectric, wherein the dielectric and the inner conductor extend distally from the outer conductor;
      a helical antenna element coaxially-disposed about a distal portion of the dielectric and coupled to the inner conductor;
      a barrel coaxially-disposed about the outer conductor and movable along a longitudinal axis thereof, the barrel having an exterior threaded portion and being coupled to the helical antenna element; and
      a rotatable adjustment collar having an interior threaded portion threadably engaged with the exterior threaded portion of the barrel,
      wherein a proximal end of the helical antenna element is coupled to a distal end of the barrel; and
   adjusting a dimension of the helical antenna element to tune the ablation probe.

5. The method for tuning an ablation probe in accordance with claim 4, wherein adjusting the dimension of the helical antenna element includes rotating the adjustment collar.

6. The method for tuning an ablation probe in accordance with claim 4, wherein the ablation probe further includes a lubricious coating on at least one of the outer conductor, the dielectric, the helical antenna element, or the barrel.

7. The method for tuning an ablation probe in accordance with claim 4, wherein a surface of the adjustment collar includes an ergonomic-enhancing element.

8. The method for tuning an ablation probe in accordance with claim 7, wherein the ergonomic-enhancing element is selected from the group consisting of scallops, protuberances, knurling, and elastomeric material.

9. A method for tuning an ablation probe, the method comprising:
   supplying energy to an ablation probe including:
      an inner conductor;
      a dielectric coaxially-disposed around the inner conductor;
      an outer conductor coaxially-disposed around the dielectric, wherein the dielectric and the inner conductor extend distally from the outer conductor;
      a helical antenna element coaxially-disposed about a distal portion of the dielectric and coupled to the inner conductor;
      a tip coupled to a distal end of the inner conductor; and
      a biasing member including a coil spring disposed about the inner conductor, the biasing member configured to bias the tip distally; and
   adjusting a dimension of the helical antenna element to tune the ablation probe.

* * * * *